（12） United States Patent
Schuldt-Hempe et al.

(10) Patent No.: US 10,433,942 B2
(45) Date of Patent: Oct. 8, 2019

(54) SURGICAL IMPLANT

(71) Applicant: Johnson & Johnson Medical GmbH, Norderstedt (DE)

(72) Inventors: Barbara Schuldt-Hempe, Bad Bramstedt (DE); Christoph Walther, Kattendorf (DE); Thorsten Deichmann, Lubeck (DE)

(73) Assignee: Johnson & Johnson Medical GmbH, Norderstedt (DE)

( * ) Notice: Subject to any disclaimer, the term of this patent is extended or adjusted under 35 U.S.C. 154(b) by 287 days.

(21) Appl. No.: 14/711,805

(22) Filed: May 14, 2015

(65) Prior Publication Data

US 2016/0058533 A1    Mar. 3, 2016

(30) Foreign Application Priority Data

Aug. 27, 2014   (DE) .......................... 10 2014 012 717

(51) Int. Cl.
*A61F 2/00* (2006.01)
*D04B 21/12* (2006.01)

(52) U.S. Cl.
CPC ............ *A61F 2/0063* (2013.01); *D04B 21/12* (2013.01); *A61F 2002/0068* (2013.01); *D10B 2509/08* (2013.01)

(58) Field of Classification Search
CPC ........... A61F 2/0063; A61F 2002/0068; D10B 2509/08
See application file for complete search history.

(56) References Cited

U.S. PATENT DOCUMENTS

| | | | |
|---|---|---|---|
| 3,682,419 A | * | 8/1972 | Vanderfaeillie ....... B21F 27/005 245/7 |
| 3,710,789 A | | 1/1973 | Ersek |
| 5,569,273 A | | 10/1996 | Titone et al. |
| 5,771,716 A | | 6/1998 | Schlussel |
| 6,120,539 A | | 9/2000 | Eldridge et al. |

(Continued)

FOREIGN PATENT DOCUMENTS

| | | |
|---|---|---|
| EP | 797962 | 9/2009 |
| RU | 2020900 C | 10/1994 |

(Continued)

OTHER PUBLICATIONS

Schumpelick, V., Klosterhafen, B., Müller, M. et al, Minimized polypropylene meshes for preperitoneal mesh plasty in incisional hernia. Chirurg. 1999;70:422-430. (Abstract in English).

(Continued)

*Primary Examiner* — Kathleen S Holwerda
*Assistant Examiner* — Christina C Lauer
(74) *Attorney, Agent, or Firm* — David R. Crichton

(57) ABSTRACT

A surgical implant comprises an areal, flexible, mesh-like basic structure (2) including a knitted fabric made in gallon crotcheting technique, in which mesh pores (4) are formed from chains (10) made in closed pillar stitch. Adjacent chains (11, 11') are connected to each other, by at least one inlaying weft thread (16, 18), in sections forming a respective common side (12) of two adjacent mesh pores (14, 14'). The inlaying weft thread (16, 18), in the region of said common side (12), runs in at least three loop courses (17, 17', 17", 19, 19', 19").

13 Claims, 3 Drawing Sheets

(56) References Cited

U.S. PATENT DOCUMENTS

Figure 1:
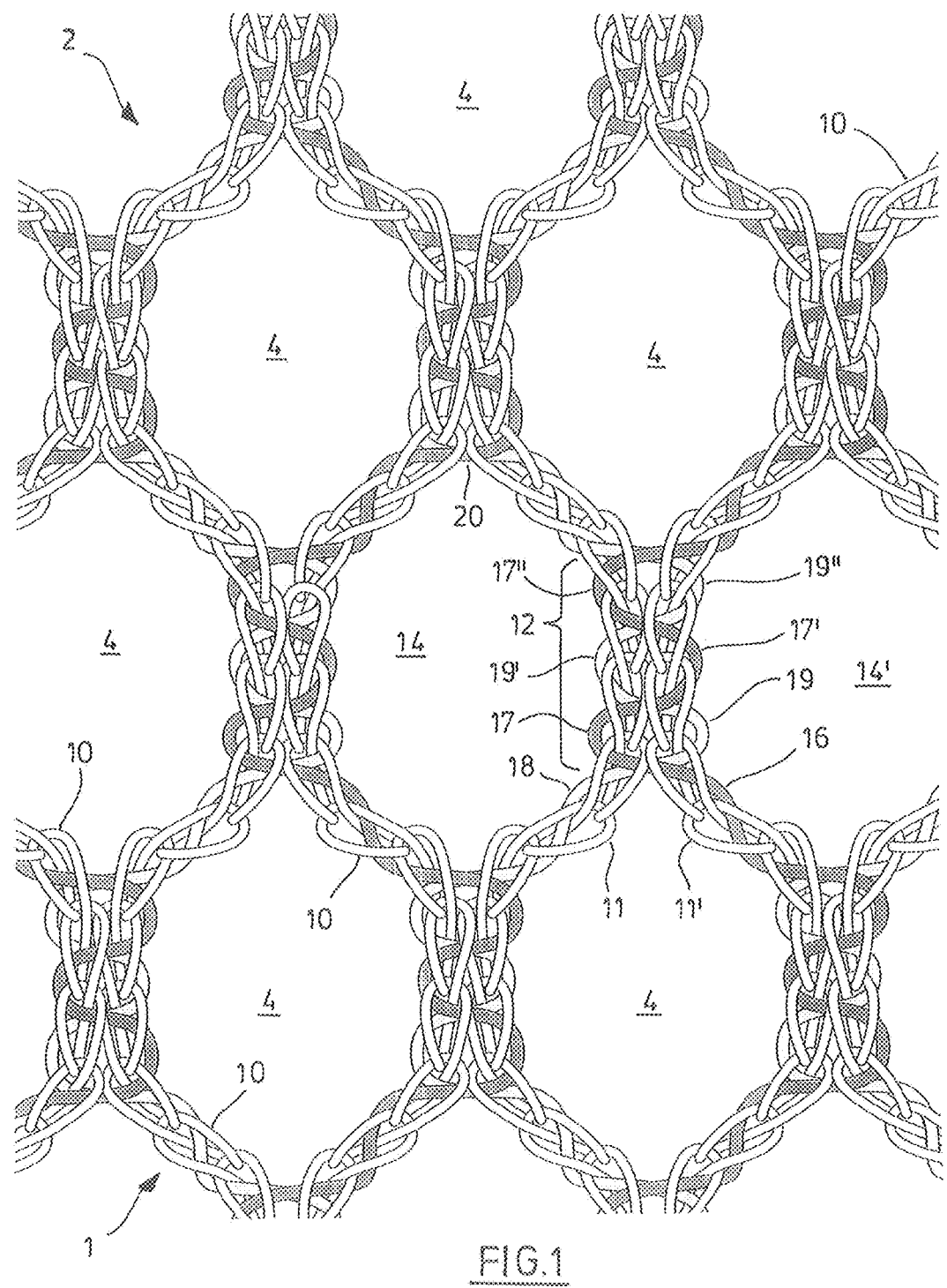

| | | |
|---|---|---|
| 6,737,371 B1 | 5/2004 | Planck et al. |
| 6,966,918 B1 * | 11/2005 | Schuldt-Hempe .... A61F 2/0063 606/151 |
| 7,614,258 B2 | 11/2009 | Cherok et al. |
| 7,900,484 B2 | 3/2011 | Cherok et al. |
| D680,649 S | 4/2013 | Jagger et al. |
| D681,813 S | 5/2013 | Jagger et al. |
| D685,476 S | 7/2013 | Jagger et al. |
| D694,886 S | 12/2013 | Jagger et al. |
| D770,046 S | 10/2016 | Harms et al. |
| D770,047 S | 10/2016 | Schneidereit et al. |
| 2004/0029478 A1 | 2/2004 | Planck et al. |
| 2004/0209538 A1 * | 10/2004 | Klinge ................. A61B 3/1015 442/59 |
| 2008/0167729 A1 | 7/2008 | Nelson et al. |
| 2008/0306494 A1 | 12/2008 | Magnusson et al. |
| 2009/0149875 A1 | 6/2009 | Abele et al. |
| 2009/0299408 A1 * | 12/2009 | Schuldt-Hempe ...... A61L 17/04 606/230 |
| 2012/0150204 A1 * | 6/2012 | Mortarino ............ A61F 2/0063 606/151 |
| 2014/0257348 A1 | 9/2014 | Priewe et al. |
| 2015/0057762 A1 | 2/2015 | Harms et al. |

FOREIGN PATENT DOCUMENTS

| | | |
|---|---|---|
| RU | 2436595 C | 12/2011 |
| WO | WO 2003/041613 A | 5/2003 |
| WO | WO 2006/092236 A | 9/2006 |
| WO | WO 2011/042811 | 4/2011 |
| WO | WO 2011/042811 A | 4/2011 |
| WO | WO 2011/159700 A | 12/2011 |

OTHER PUBLICATIONS

International Search Report dated Oct. 8, 2015, for international application PCT/EP2015/001588.

International Preliminary Report on Patentability dated Mar. 9, 2017, for international application PCT/EP2015/001588.

* cited by examiner

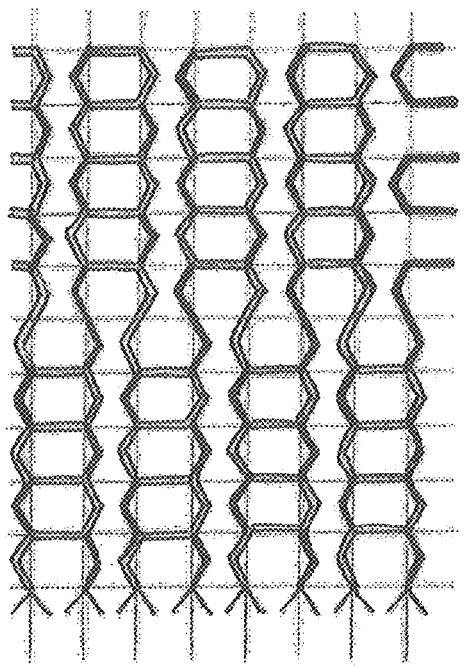
(a)
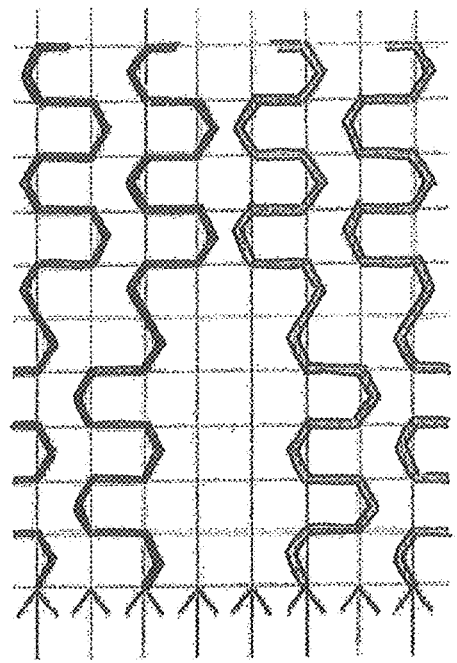
(b)
FIG.3
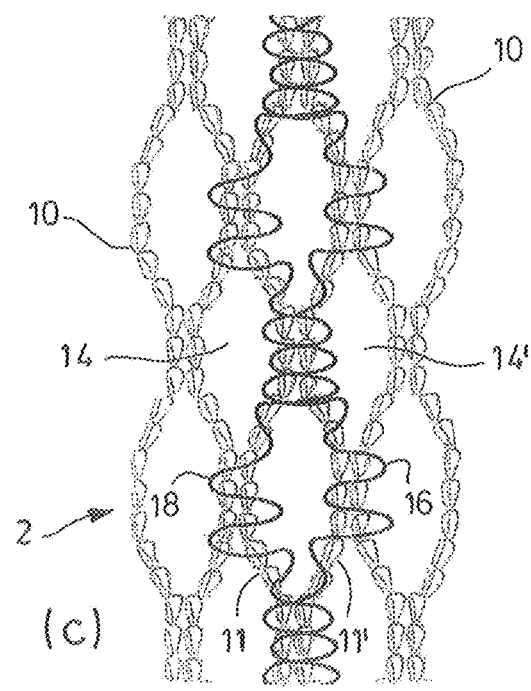
(c)

SURGICAL IMPLANT

CROSS REFERENCE TO RELATED APPLICATIONS

This application claims priority from German Patent Application DE 102014012717.6 filed Aug. 27, 2014 the disclosure of which is hereby incorporated by reference in its entirety.

The invention relates to a surgical implant, in particular for abdominal wall closure.

Hernia repair is one of the most common surgical procedures, with approximately 6.4 million procedures performed globally every year. Annually, approximately 3.1 million hernias (48%) are repaired by means of a flat mesh.

It is known to use implant meshes in hernia repair made from the non-absorbable (non-resorbable) plastics materials polypropylene or polyester or from the slowly absorbable (resorbable) materials polyglactin 910 (a copolymer of glycolide and lactide in the ratio 9:1) or polyglecaprone (a copolymer of glycolide and caprolactone) or from combinations of non-absorbable materials and absorbable materials.

The known mesh implants have some disadvantages, however. For example, they are relatively heavy, i.e. the areal weight is, as a rule, more than 50 g/m² and predominantly even about 100 g/m². Thus, if the implants are not absorbable, a relatively large quantity of foreign substance remains permanently in the body.

These properties can affect the comfort and mobility of a patient who is fitted with such an implant. Moreover, this type of mesh generally includes relatively small pores, which has the drawback of bridging formation.

Another drawback of known mesh implants is a high anisotropy, in particular if the implants comprise a knitted textile structure. That means, e.g., the force-elongation behavior or the tear behavior in different draw directions (as measured in a uniaxial stripe tensile test) is generally much different.

Anisotropies are also present in the so-called "suture pull-out strength". As a result of this, problems with fixation of the implants may occur because a suture may pull out of the mesh, resulting in a dislocation. Another problem with the anisotropic behavior of known implants is the collapse of mesh pores after uniaxial or punctual stress. High stress leads to a reduction of the so-called effective pore surface, which may result in an excessive foreign body reaction and subsequently in bridging formation.

Some known implants are partly absorbable (e.g., Ultrapro® of Ethicon, Vypro® of Ethicon, Vypro® II of Ethicon, Seramesh® of Serag Wiessner) in order to overcome the drawback of the heavy-weight meshes (e.g., Marlex® mesh of Bard, Prolene® mesh of Ethicon) because, after absorption of the absorbable part, the areal weight is relatively low. However, for these types of implant meshes, the remaining suture pull-out strength after absorption of the absorbable part of the mesh tends to be small.

EP 0 797 962 A discloses a light-weight areal implant, in particular for abdominal wall closure, including a flexible basic structure made from a knitted fabric comprising non-absorbable or slowly absorbable material or a combination of such materials. The knitted fabric of the basic structure is designed to stretch more than the tissue region destined to receive the implant below a critical force and stretch less than this tissue region above the critical force. The critical force lies below the highest load which is allowable for this tissue region. The basic structure is provided with a stiffening, synthetic absorbable material having a shorter absorption time than that of the basic structure. This implant is marketed by Ethicon as Vypro®.

WO 2011/042811 A describes isoelastic porous implant meshes useful in hernia repair having pores that remain open under physiological loads.

The properties of prior art polypropylene implant meshes for hernia repair are compared by V. Schumpelick et al. in Chirurg 70, 422-430 (1999).

Implant meshes having a generally hexagonal or honeycomb-like shape of the mesh pores are disclosed in U.S. Pat. No. 6,737,371, US 2009/0149875 A, U.S. Pat. Nos. 7,900,484, and 5,569,273.

The object of the invention is to provide a surgical implant, in particular for abdominal wall closure, which exhibits relatively isotropic mechanical properties, in particular with respect to suture pull-out strength.

This object is achieved by a surgical implant having the features of claim 1. Advantageous versions of the invention follow from the dependent claims.

The surgical implant according to the invention comprises an areal, flexible, mesh-like basic structure including a knitted fabric made in gallon crotcheting technique. In this fabric, mesh pores are formed from chains (generally in warp direction) made in closed pillar stitch. Adjacent chains are connected to each other, by at least one inlaying weft thread, in sections forming a respective common side of two adjacent mesh pores. The inlaying weft thread, in the region of said common side, runs in at least three loop courses. More than three loop courses are also possible, e.g. five or seven loop courses.

The term "areal" means that the basic structure is a generally flat structure, which may be curved into the third dimension, however. Moreover, the basic structure may be folded, e.g., to form pockets. The implant may consist of the basic structure only, but additional components (e.g. a film attached to the basic structure, etc.) are conceivable as well. A blank of the basic structure may have any shape. A basic structure constituted of more than one part is also possible.

The common side of two adjacent mesh pores of the basic structure is well stabilized by the at least three loop courses, better than in the case of the mesh pores of the prior art Ultrapro® implant which uses only one loop course resulting in a more point-like connection between adjacent mesh pores. If a suture laid through a mesh pore of the surgical implant according to the invention is pulled in a direction generally perpendicularly to this common side, the closed pillar stitch structure of the chains will be strong enough to resist suture pull-out due to rupture of the material of the mesh pore in question. And if the suture is pulled in a direction generally in parallel to this common side, i.e. in warp direction, the region of the common side will resist rupture as well because it is held together by the at least three loop courses. In contrast thereto, the Ultrapro® implant would not well resist pulling in warp direction.

Thus, the suture pull-out strength in the surgical implant according to the invention behaves largely isotropic (in the area of the basic structure) and can be high, and the mechanical properties of the implant generally tend to be isotropic. Suture pull-out with the result of a dislocation of the mesh pores including a distortion of the implant or even a dislocation of the implant as a whole are no problems anymore. The implant can be easily fixed in a surgical procedure.

Generally, the surgical implant according to the invention has enhanced handling properties and resistance to tearing when compared to prior art light-weight meshes (e.g., an Ultrapro® implant). Additionally, an improved elasticity (more isotropic stretch behavior in course and wale direction of the mesh structure) improves the adaption to anatomical conditions.

The surgical implant according to the invention is well suited for hernia repair. Other applications, e.g. as pelvic meshes or breast implants, are conceivable as well.

Said adjacent chains, at a respective common side of two adjacent mesh pores, may be connected by two inlaying weft threads, one generally following one of the chains and the other one generally following the other one of the chains, wherein each of the two inlaying weft threads, in the region of said common side, runs in at least three loop courses. Thus, e.g., there is one inlaying weft thread coming from the left and one inlaying weft thread coming from the right, forming generally a mirror symmetry, and the total number of loop courses in the region of the common side is greater than with one inlaying weft thread only, which improves the overall stability of the implant.

As a result of the textile technique described so far, the mesh pores of the mesh-like basic structure may have a generally hexagonal shape. This is advantageous in terms of generally isotropic properties of the implant.

In advantageous embodiments of the invention, the suture pull-out strength measured in a direction generally in parallel to said common side of two adjacent mesh pores (i.e. generally in warp direction) and the suture pull-out strength measured in a direction generally perpendicularly thereto may differ by at most 20% only, related to the greater one of these suture pull-out strength values. A test for measuring the suture pull-out strength is described further below. Shortly, a sample of the basic structure is fixed to a load cell, at one side, by three suture loops and stretched until a mesh pore of the basic structure crossed by one of these suture loops ruptures.

The basic structure of the surgical implant according to the invention may comprise non-absorbable material or slowly absorbable material or a combination of such materials. In this context, slowly absorbable material is defined as an absorbable material having an absorption time of at least 60 days or an in-vivo decrease in strength leading to a tearing strength after 30 days which is at least 10% of the initial tearing strength. The presence of non-absorbable or slowly absorbable material ensures that the basic structure is stable in the longer term and improves the healing success.

Alternatively or additionally, the basic structure may comprise absorbable material. The absorbable material can provide strength or additional strength during the initial healing process. Later on, when a reinforcement effect of the implant is less important, the absorbable material is decomposed in the environment provided by bodily tissue so that the absorbable material finally disappears. Even if the absorbable material does not much contribute to the strength of a basic structure which also comprises non-absorbable material, the absorbable material may improve the handling properties of the implant during the surgical procedure or it may enhance the initial healing process.

Generally, non-absorbable or slowly absorbable materials for the basic structure are well known in the art. Suitable non-absorbable substances include, e.g., polyolefins (e.g. polypropylene (Prolene® of Ethicon) or polyethylene), fluorinated polyolefines (e.g. polytetrafluoroethylene (PTFE) or polyvinylidene fluoride), blends of polyvinylidene fluoride and co-polymers of vinylidene fluoride and hexafluoropropene (e.g. Pronova® of Ethicon), and polyesters. An example for slowly absorbable materials are copolymers of glycolide and lactide in the ratio 5:95 coated with a copolymer of caprolactone and glycolide (e.g. Panacryl® of Ethicon). Further examples for non-absorbable materials are polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimides, etc. Mixtures and/or co-polymers of such substances are conceivable as well.

Absorbable materials are also well known in the art. Examples are poly-p-dioxanone (PDS® of Ethicon), copolymers of glycolide and lactide (in particular in the ratio 90:10, Vicryl® of Ethicon) and copolymers of glycolide and ε-caprolactone (Monocryl® of Ethicon). Further examples are polyhydroxy acids, polylactides, polyglycolides, copolymers of lactide and trimethylene carbonate, copolymers of glycolide, lactide and trimethylene carbonate, polyhydroxybutyrates, polyhydroxyvaleriates, polycaprolactones, etc., including mixtures and/or co-polymers thereof. The selection of the material depends, e.g., on the resorption period in bodily tissue or an appropriate in-vitro medium.

For example, the basic structure of the surgical implant according to the invention may comprise threads twisted from filaments made of non-absorbable or slowly absorbable material or mixtures thereof and from filaments made of absorbable material. In this case, the basic structure can be made from such threads in crotchet technique. Some time after implantation, the absorbable filaments will have been absorbed, but the general shape of the implant and the isotropy of its properties will remain.

If the basic structure comprises non-absorbable (and/or slowly absorbable) material as well as absorbable material, it is possible to design the implant such that its strength is mainly determined by the non-absorbable (and/or slowly absorbable) material. For example, after implantation and after decomposition of the absorbable material, at least one of the suture pull-out strengths measured in a direction generally in parallel or perpendicularly to the common side of two adjacent mesh pores may differ from the respective initial value by less than 25% only, related to the respective initial value. In this case, the reduction in suture pull-out strength is of minor importance only. For test purposes, the state after decomposition of the absorbable material can be achieved in-vitro by incubation of the implant in a suitable buffer.

In advantageous embodiments of the invention, both the suture pull-out strengths measured in a direction generally in parallel to the common side of two adjacent mesh pores of the basic structure and measured in a direction generally perpendicularly to this common side are at least 15 N, related to one suture loop crossing one mesh pore and measured before implantation. Such values are sufficient for a safe fixation of the implant and can be easily achieved even for light-weight basic structures, in view of the largely isotropic behavior of the basic structure discussed above. The test for measuring suture pull-out strengths has already been mentioned above and will be described in more detail further below.

Preferably, the mesh pores of the mesh-like basic structure have an individual pore size (free area) of at least 3 $mm^2$.

This is relatively large, generally results in a low-weight structure and overcomes the drawback of excessive foreign body reaction including a subsequent "bridging formation".

The surgical implant according to the invention may comprise colored markings. Such markings provide an aid to a surgeon when handling the implant. In advantageous embodiments, at least one pair of adjacent chains made in closed pillar stitch has a color different from the majority of the chains. In this way, a pattern of parallel stripes can be formed, which may be arranged in an equidistant manner or with different distances.

In the following, the invention is described in more detail by means of an embodiment. The drawings show in FIG. 1 a magnified top view of part of the basic structure in an embodiment of the surgical implant according to the invention, FIG. 2 a magnified bottom view of part of the basic structure according to FIG. 1, and FIG. 3 schematic illustrations of the fabric construction of the basic structure according to FIGS. 1 and 2, i.e. in part (a) a schematic representation of the combined movement of the bars used for laying inlaying weft threads in gallon crotcheting technique, in part (b) a schematic illustration of the individual movements of these bars, and in part (c) an illustration of the resulting connections at respective common sides of two adjacent mesh pores.

FIG. 1 illustrates part of a basic structure of an embodiment of a surgical implant 1 in a magnified top view. The basic structure, designated by 2, is designed as a knitted fabric made in gallon crotcheting technique. The pattern shown in FIG. 1 extends beyond the boundaries of the figure and, in the embodiment, repeats in the same manner. The basic structure 2 forms a flexible surgical mesh which comprises a plurality of mesh pores 4. In the embodiment, the size of one mesh pore (free area of the corresponding opening) is about 4 mm$^2$.

The mesh pores 4 are determined by chains 10 made in closed pillar stitch, as well known in gallon crotcheting technique. In the orientation of FIG. 1, the chains 10 generally extend from bottom to top of the figure and undulate back and forth in a direction running transversally thereto.

The chains 10 of a randomly selected pair of adjacent chains are designated by 11 and 11'. In a section indicated in FIG. 1 by a curved bracket, the chains 11 and 11' form the common side 12 of two adjacent mesh pores 14 and 14'. In the region of this common side 12, the adjacent chains 11 and 11' are connected by an inlaying weft thread 16, which runs in three loop courses 17, 17' and 17", and by another inlaying weft thread 18, which also runs in three loop courses 19, 19' and 19". For clarification purposes, the inlaying weft thread 16 is represented in dark grey, whereas the inlaying weft thread 18 is represented in a medium grey grade. The inlaying weft threads 16 and 18 generally follow the chains 11' and 11, respectively, along mirror-like paths, and participate in the connection of a plurality of respective pairs of adjacent mesh pores 4 in addition to the mesh pores 14 and 14'.

It is evident from FIG. 1 that other chains 10 form respective common sides of adjacent mesh pores 4 as well, wherein these common sides are connected by two inlaying weft threads, each one forming three loop courses in the region of the common side in question. This construction in gallon crotcheting technique results in safe interconnections in the mesh-like basic structure 2 of the surgical implant 1.

When a suture loop is laid through one mesh pore 4, close to the plane of paper in FIG. 1 the suture may extend approximately perpendicularly to the plane of paper. When this suture is pulled to the top side of FIG. 1, it will tend to exert forces onto the basic structure 2 in an engagement zone 20 so that it may try to enter the region of a respective common side 12. In this region, however, the adjacent chains 11 and 11' are safely connected to each other because the inlaying weft threads 16, 18 participating in the connection each form three loop courses 17, 17', 17" and 19, 19', 19", respectively (and not just one). When the suture is pulled in another direction, it hits the material of the basic structure 2 transversely to a respective direction of a chain 10, which tends to be not critical because of the generally strong closed pillar stitch structure of the chains 10. Consequently, the suture pull-out forces can be high in all directions, wherein the absolute values of the suture pull-out forces depend on the selected material of the basic structure 2.

Figure 2:
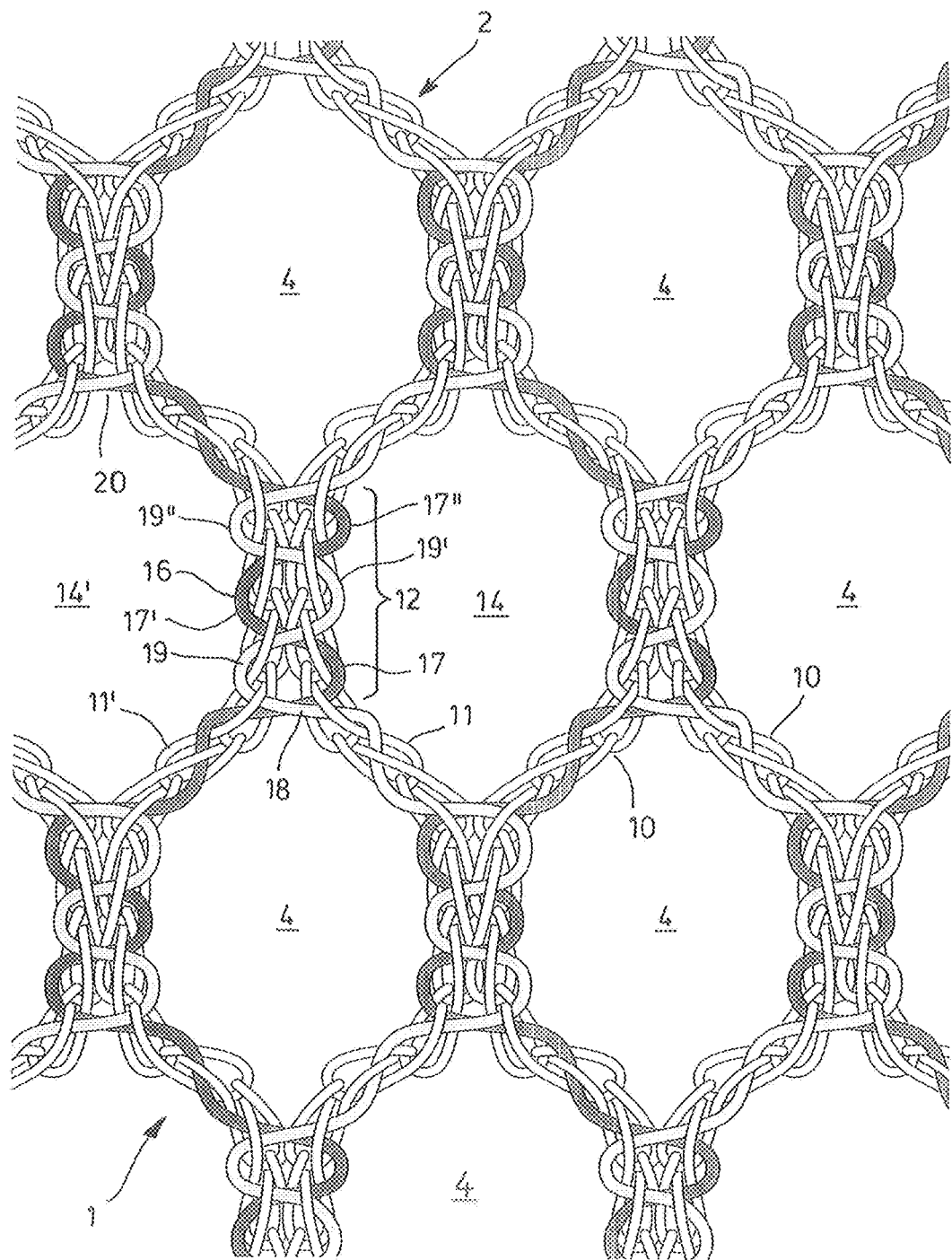

FIG. 2 is a view similar to FIG. 1 and shows the basic structure 2 from the bottom side, wherein the terms "top" and "bottom" are arbitrary, however. FIG. 2 is essentially a mirror view of FIG. 1.

EXAMPLE

In an example, a basic structure as generally shown in FIGS. 1 and 2 was manufactured.

FIG. 3 illustrates, in a schematic manner familiar to a person skilled in fabric manufacturing, how the basic structure 2 of FIGS. 1 and 2 was knitted in gallon crotcheting technique. FIG. 3(a) is a schematic representation of the combined movement of the bars used for laying the inlaying weft threads 16, 18, and FIG. 3(b) is a schematic illustration of the individual movements of these bars. FIG. 3(c) shows the resulting connections at respective common sides 12 of two adjacent mesh pores 14, 14' and is similar to FIGS. 1 and 2.

Using the terms familiar to the skilled person, the basic structure 2 of the embodiment was warp-knitted in gallon crotcheting technique on a chrochet machine, type ACO-TRONIC of the company Comez, Italy.

Pattern in the embodiment:
Basic system of warp threads:
Closed-lap pillar stitch (chains 10)
Movement of two guide bars for weft threads (inlaying weft threads 16, 18):
Bar 1: 3-1/3-1/3-2/4-2/4-2//
Bar 2: 2-4/2-4/2-3/1-3/1-3//

In the example, the material used for the chains 10 made in closed pillar stitch and for the inlaying weft threads 16 and 18 was a twisted thread comprising one non-absorbable monofilament of polypropylene (Prolene® of Ethicon; diameter 3.5 mil=88.9 μm) and one absorbable monofilament of polyglecaprone (Monocryl® of Ethicon; diameter 5 mil=127 μm). The twisting was performed on an Uptwister of the company Lezzini TBR, Italy, with the first twisting step in S-direction/155 T/m and the second twisting step in Z-direction/175 T/m.

This thread material was partially absorbable. After decomposition of the absorbable component, the basic structure 2 had essentially the same set-up as before decomposition, and its strength had not much decreased (see below). The absorbable component was nevertheless important because it improved the handling properties of the surgical implant 1 and it had advantageous effects on the initial healing process after implantation.

In the example, a large-area basic structure 2 was cut into individual sheets of appropriate size to constitute individual surgical implants. These sheets were clamped on a temper frame and annealed for 9 hours at 113° C.

The following Table 1 displays the suture pull-out strengths and the pore sizes for several mesh implants of the prior art (Vypro®, Vypro II® and Ultrapro® of Ethicon, Seramesh® of Serag Wiessner) and for several samples (Run 1 to Run 7) of the basic structure 2 according to the example described so far.

The samples of Run 1 to Run 7 were produced under the same process conditions with slight differences in the thread tension of the warp thread for the closed pillar stitch, the inlaying weft thread and the take of the mesh material. Such differences occurred under usual manufacturing conditions and were not expected to significantly influence the suture pull-out strengths, which was verified by the relatively small variation of the results for Run 1 to Run 7 presented in Table 1.

The method of measuring the suture pull-out strengths is explained below. The numerical values for the suture-pull out strengths in Table 1 all relate to three sutures so that they have to be divided by three in order to obtain values for a single suture. "Vertical" means the direction left-right and "Horizontal" the direction up-down in FIGS. 1 to 3. The pore width and length refers to the respective distances between the centers of the threads bordering the pore in question. The free area is the open area of a pore, without any bordering material.

The initial suture pull-out strengths were measured with mesh implants as sold (prior art) and implants after preparation as described above (Run 1 to Run 7), respectively. To obtain degraded meshes with the absorbable component decomposed and removed from the mesh, the respective implants were incubated for 10 days in a buffer solution of pH 7.26 at 55° C.

direction (i.e. the up-down direction in FIGS. 1 and 2) and in transverse (weft) direction (i.e. the left-right direction in FIGS. 1 and 2). Samples representing the state after degradation of the absorbable component were prepared in a buffer solution, as described above.

The testing machine comprised a load cell (2.5 kN) for exerting tensile forces, wherein an upper gripping jaw could be moved away from a lower gripping jaw, starting with a clamping length of 100 mm and a pre-load force of 0.3 N and running with a pulling speed of 30 mm/min.

A sample to be tested was turned to the desired orientation and was provided with three suture loops at its upper edge and three suture loops at its lower edge. To this end, the suture loops were laid through the free area of a respective mesh pore so that their free ends extended beyond the respective edge of the sample. For the suture loops, Prolene® #2-0 (Ethicon; polypropylene monofilament having a diameter of 0.3 mm) was used. In each one of the upper and lower edge regions, the distance between two adjacent Prolene® sutures was 10 mm and the distance of a Prolene® suture to the nearest edges of the sample was 15 mm. The suture loops were slightly fixed to the sample by means of an adhesive tape, which did not affect the test results, however.

The free ends of the Prolene® sutures (i.e. the suture ends extending beyond the sample) were clamped to the upper

TABLE 1

Suture pull-out strengths and pore sizes for several implants of the prior art and for the basic structure described above (Run 1 to Run 7)

| | | Suture pull-out strength | | | | | | | | | Pore size | |
| | | Initial | | | After degradation | | | Difference | | | Width × length | |
| | Implant (mesh) | Vertical [N] | Horizontal [N] | Difference [%] | Vertical [N[ | Horizontal [N] | Difference [%] | Vertical [%] | Horizontal [%] | Average [%] | (center-center) [mm × mm] | Free area [mm$^2$] |
| --- | --- | --- | --- | --- | --- | --- | --- | --- | --- | --- | --- | --- |
| Prior art (trade marks) | Vypro | 68.09 | 46.53 | 31.66 | 26.91 | 23.34 | 13.27 | 60.48 | 49.84 | 55.16 | 3.6 × 3.9 | 7 |
| | Vypro II | 74.38 | 45.51 | 38.81 | 32.82 | 30.24 | 7.86 | 55.88 | 33.55 | 44.71 | 2.3 × 2.7 | 4 |
| | Ultrapro | 82.38 | 56.89 | 30.94 | 41.11 | 38.57 | 6.18 | 50.10 | 32.20 | 41.15 | 2.4 × 3.0 | 3.7 |
| | Sera-mesh | 72.76 | 74.01 | 1.72 | 51.38 | 48.43 | 5.74 | 29.38 | 34.56 | 31.97 | 1.9 × 2.2 | 2 |
| Invention | Run 1 | 68.83 | 66.27 | 3.72 | 59.15 | 63.06 | −6.61 | 14.06 | 4.84 | 9.45 | 2.3 × 3.0 | 4 |
| | Run 2 | 75.60 | 73.00 | 3.44 | 60.86 | 63.79 | −4.81 | 19.50 | 12.62 | 16.06 | | |
| | Run 3 | 66.66 | 60.17 | 9.74 | 49.75 | 58.46 | −17.51 | 25.37 | 2.84 | 14.10 | | |
| | Run 4 | 68.12 | 64.95 | 4.65 | 57.06 | 56.55 | 0.89 | 16.24 | 12.93 | 14.58 | | |
| | Run 5 | 73.12 | 68.33 | 6.55 | 61.43 | 67.44 | −9.78 | 15.99 | 1.30 | 8.64 | | |
| | Run 6 | 58.29 | 65.58 | 12.51 | 54.60 | 66.54 | −21.87 | 6.33 | −1.46 | 2.43 | | |
| | Run 7 | 71.21 | 65.58 | 7.91 | 71.21 | 65.58 | 7.91 | 0.00 | 0.00 | 0.00 | | |

Table 1 shows that the implants of Run 1 to Run 7 largely behaved isotropic, i.e. the suture pull-out strength did not much depend on the direction (vertical or horizontal), both before and after degradation. In particular and in contrast to some of the prior-art implants, the suture pull-out strength in "horizontal" direction (i.e. in parallel to the respective common side 12 in FIGS. 1 and 2) was almost as high as that in the direction perpendicular thereto. Moreover, in the implants of Run 1 to Run 7, the suture pull-out strengths did not much deteriorate upon degradation, in contrast to the mesh implants of the prior art.

The suture pull-out strength in the meshes of Table 1 were measured by means of a test method developed in accordance to the standard DIN 53857 (stripe testing of fabrics). This standard was modified to mimic the strength relation between bodily tissue, suture material and implant mesh.

To run a test, a mesh sample having a size of 5.0 cm×5.0 cm was used. The samples were cut in longitudinal (warp)

gripping jaw and to the lower gripping jaw, respectively, starting with the upper gripping jaw. They had to be fixed in such a way that they pulled on the sample with an equal tension during the test.

Thereafter, the testing machine was started and the jaws pulled at the sample until the first one of the Prolene® sutures ruptured the mesh structure of the sample. This was the respective suture pull-out strength value given in Table 1.

Generally, there are many possibilities for the construction and design of the surgical implant and its basic structure and for the choice of material. Many examples for non-absorbable and absorbable materials are disclosed in the introductory part of the description.

The invention claimed is:
1. A surgical implant, comprising an areal, flexible, mesh-like basic structure including a knitted fabric made in gallon crotcheting technique, in which generally hexagonal shaped mesh pores are formed from chains made in closed pillar stitch, wherein adjacent chains of adjacent pores are connected to each other, by at least one inlaying weft thread, in sections forming a respective common side of two adjacent hexagonal mesh pores, characterized in that the inlaying weft thread, in the region of said common side, runs in at least three loop courses comprising at least three loops, wherein each of the three loops of the three loop courses pass through both of the adjacent chains of adjacent pores that form an adjacent side.

2. A surgical implant according to claim 1, characterized in that said adjacent chains are connected by two inlaying weft threads, one generally following one of the chains and the other one generally following the other one of the chains, wherein each of the two inlaying weft threads, in the region of said common side, runs in at least three loop courses.

3. A surgical implant according to claim 1, characterized in that a suture pull-out strength measured in a direction generally in parallel to said common side of two adjacent mesh pores and a suture pull-out strength measured in a direction generally perpendicularly to said common side of two adjacent mesh pores differ by at most 20%, related to the greater one of these suture pull-out strength values.

4. A surgical implant according to claim 1, characterized in that the basic structure comprises non-absorbable material, or slowly absorbable material defined as having an absorption time of at least 60 days or an in-vivo decrease in strength leading to a tearing strength after 30 days which is at least 10% of the initial tearing strength, or a combination of such materials.

5. A surgical implant according to claim 4, characterized in that the basic structure comprises threads twisted from filaments made of non-absorbable or slowly absorbable material or mixtures thereof and from filaments made of absorbable material.

6. A surgical implant according to claim 4, characterized in that the basic structure comprises absorbable material and in that, after decomposition of the absorbable material, at least one of a suture pull out strength measured in a direction generally in parallel or a suture pull-out strength measured in a direction generally perpendicularly to said common side of two adjacent mesh pores differs from the respective initial value by less than 25%, related to the respective initial value.

7. A surgical implant according to claim 4, characterized in that the non-absorbable or slowly absorbable material comprises at least one of the substances included in the following list: polyolefins, polypropylene, fluorinated polyolefines, blends of polyvinylidene fluoride and copolymers of vinylidene fluoride and hexafluoropropene, polyesters, and copolymers of glycolide and lactide in the ratio 5:95.

8. A surgical implant according to claim 1, characterized in that the basic structure comprises absorbable material.

9. A surgical implant according to claim 8, characterized in that the absorbable material comprises at least one of the substances included in the following list: poly-p-dioxanone, copolymers of glycolide and lactide, copolymers of glycolide and lactide in the ratio 90:10, copolymers of glycolide and ε-caprolactone.

10. A surgical implant according to claim 1, characterized in that both a suture pull-out strength measured in a direction generally in parallel to said common side of two adjacent mesh pores and a suture pull-out strength measured in a direction generally perpendicular said common side of two adjacent mesh pores are at least 15 N, related to one suture loop crossing one mesh pore and measured before implantation.

11. A surgical implant according to claim 1, characterized in that the mesh pores of the mesh-like basic structure (2) have an individual pore size of at least 3 mm$^2$.

12. A surgical implant according to claim 1, characterized by colored markings.

13. A surgical implant according to claim 12, characterized in that at least one pair of adjacent chains made in closed pillar stitch has a color different from a majority of the chains made in closed pillar stitch.

* * * * *